United States Patent
Kobayashi (10) Patent No.: US 8,238,012 B2
(45) Date of Patent: Aug. 7, 2012

(54) OPTICAL IMAGE-CAPTURING APPARATUS

(75) Inventor: Koji Kobayashi, Tokyo (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 13/138,218

(22) PCT Filed: Jan. 20, 2010

(86) PCT No.: PCT/JP2010/050584
§ 371 (c)(1),
(2), (4) Date: Jul. 20, 2011

(87) PCT Pub. No.: WO2010/087251
PCT Pub. Date: Aug. 5, 2010

(65) Prior Publication Data
US 2011/0273757 A1    Nov. 10, 2011

(30) Foreign Application Priority Data
Jan. 30, 2009  (JP) .................. 2009-019831

(51) Int. Cl.
*G02B 26/08* (2006.01)
(52) U.S. Cl. .................. 359/201.1; 359/201.2; 250/234
(58) Field of Classification Search .... 359/201.1–201.2, 359/204.1–204.5; 250/234–236
See application file for complete search history.

(56) References Cited

U.S. PATENT DOCUMENTS
2007/0263171 A1 * 11/2007 Ferguson et al. ............. 351/206

FOREIGN PATENT DOCUMENTS

| JP | 10332329 | 12/1998 |
|----|----------|---------|
| JP | 2002095663 | 4/2002 |
| JP | 2003227796 | 8/2003 |
| JP | 2007252693 | 10/2007 |
| JP | 2008237237 | 10/2008 |
| JP | 2008309613 | 12/2008 |
| WO | 2007041382 | 4/2007 |

* cited by examiner

Primary Examiner — James Phan
(74) Attorney, Agent, or Firm — Adams & Wilks (57) ABSTRACT

Light beams from light sources 1, 2 are scanned by a galvano mirror 10a to illuminate a predetermined portion 15b of an object to be observed 15 via an objective lens 14. The reflected light from the object is re-scanned by the galvano mirror 10a to obtain a two-dimensional image via an image-capturing element 25. Measuring means composed of an OCT interferometer 32 is branched or coupled in the optical path between the objective lens 14 and the galvano mirror 10a to obtain a tomographic image of the object. In this configuration, the two-dimensional image and the tomographic image of the object can be displayed simultaneously on a display device 28.

4 Claims, 4 Drawing Sheets

OPTICAL IMAGE-CAPTURING APPARATUS

CROSS-REFERENCE TO RELATED APPLICATIONS

This application is a U.S. national stage application of International Application No. PCT/JP2010/050584 filed Jan. 20, 2010, claiming a priority date of Jan. 30, 2009, and published in a non-English language.

TECHNICAL FIELD

The present invention relates to an optical image-capturing apparatus, and more specifically to an optical image-capturing apparatus in which a light beam from a light source is scanned to illuminate a predetermined portion of an object to be observed, and reflected light or fluorescent light from the object is received to obtain two-dimensional image information of the object.

BACKGROUND ART

As is well known, optical image-capturing apparatuses using light beam scanning can observe high-contrast/high-resolution image information based on reflected light or fluorescent light from an object to be observed. As a result, they are particularly useful in the observation of low-contrast objects. Widely used examples include scanning laser microscopes (SLM) in biological and industrial fields and medical applications such as scanning laser ophthalmoscopes (SLO) in the field of ophthalmology.

A technology related to SLM or SLO is, e.g., a scanning method using a slit beam, which reduces the burden associated with the high-speed operation of the light scanning means and which is both highly economical and practical because the object can be imaged in real time. The following is known of this technology.

Patent Document 1 discloses a configuration for an optical microscope in which a slit-shaped light beam is scanned by the first surface of a rotating mirror to illuminate an object to be observed, and reflected light from the object to be observed is scanned using the second and third surfaces of the rotating mirror and received by a predetermined detector array.

Patent Document 2 discloses a configuration for a scanning ophthalmoscope in which a light beam shaped so as to converge linearly on the focal plane is scanned one-dimensionally to illuminate the ocular fundus of an eye to be examined, and reflected light from the ocular fundus is received via scanning means by a photodetector array corresponding to the convergence line of the light beam.

Patent Document 3 discloses a configuration for a scanning laser ophthalmoscope in which a light beam in the shape of a line is scanned one-dimensionally in the direction orthogonal to the direction of the line to illuminate an eye to be examined, and reflected light from the eye to be examined is received by a one-dimensional linear CCD array detector corresponding to the line direction of the light beam.

Patent Document 4 discloses a configuration for an ophthalmoscope in which a slit-shaped light beam is scanned by the first surface of a rotating mirror to illuminate the ocular fundus of an eye to be examined, and reflected light from the ocular fundus is scanned by the second and third surfaces of the rotating mirror and received by an array-type photodetector such as a predetermined CCD or CMOS sensor.

Non-Patent Document 1 discloses a basic configuration of a scanning confocal microscope including a scanning optical system using the obverse side and reverse side of an oscillating mirror and detecting the specular reflection of a slit-shaped light beam. The ability of this configuration to observe clear corneal tissue cells in real time with high contrast has been demonstrated experimentally.

A device which combines the technology of SLMs and SLOs scanning optical systems with the technology of interference optical systems has recently garnered attention in the fields of medicine and biology. This device is an image-capturing apparatus for tomographic information (optical coherence tomography or OCT) that uses the interference phenomenon of low-interference light beams (partially coherent light). Many technologies related to OCT have been presented. The following are some examples.

Patent Document 5 discloses an OCT configuration including an interferometer using a light source having short coherence length characteristics and an optical fiber, horizontal scanning means arranged in the optical path of probe light directed towards a sample material, and the like. The basic technology for generating a tomographic image of the sample material is disclosed in this patent document.

Patent Document 6 discloses a configuration in which the light beam is split into a reference arm and a measurement arm, and a spectroscope detects the intensity of light that appears as interference between measurement light via the measurement arm and reference light via the reference arm. This patent document discloses a configuration in which an arithmetic operation such as a Fourier transform is performed on detected signals obtained via the spectroscope to thereby allow optical tomography of transparent, partially transparent, and opaque objects.

Patent Document 7 discloses a measurement device composed of an interferometer and a spectrometer wherein the light beam from a light source is condensed linearly relative to an object to be measured, and observed light from the object to be measured is detected via the spectrometer by a two-dimensional image sensor. An arithmetic operation such as a Fourier transform is performed on the detected signals from the image sensor, and tomographic information on the object to be measured is obtained at high speed in accordance with the computational speed.

Patent Document 8 proposes an OCT configuration including an interferometer, light modulating means, light scanning means, re-scanning means, and two-dimensional image-capturing means. In this configuration, it is shown that reflection intensity information from the interior of an object can be obtained at high speed by properly processing the interference information detected from the output signals of the image-capturing means.

Non-Patent Document 2 discloses a configuration for a device combining a line scanning laser ophthalmoscope (LSLO) using a one-dimensional CCD array sensor as a detector and a spectral domain OCT (SDOCT) using an optical fiber interferometer. In this configuration, it is empirically shown that two-dimensional reflection images or tomographic images in the depth direction of the ocular fundus to be observed can be selectively imaged using a single device.

PRIOR ART DOCUMENTS

Patent Documents

Patent Document 1: U.S. Pat. No. 4,241,257
Patent Document 2: U.S. Pat. No. 4,768,874
Patent Document 3: U.S. Pat. No. 6,758,564
Patent Document 4: U.S. Pat. No. 7,331,669
Patent Document 5: PCT (WO) 6-511312 (Japanese Patent No. 3479069)

Patent Document 6: Japanese Laid-open Patent Publication No. 11-325849

Patent Document 7: Japanese Laid-open Patent Publication No. 2006-116028

Patent Document 8: Japanese Laid-open Patent Publication No. 2008-309613

Non-Patent Documents

Non-Patent Document 1: Article, Applied Optics, Vol. 33 (1994), No. 4, pp. 695-701, "Real-time scanning slit confocal microscopy of the in vivo human cornea" (B. R. Masters and A. A. Thaer)

Non-Patent Document 2: Article, Optics Express, Vol. 14 (2006), No. 26, pp. 12909-12914, "Hybrid retinal imager using line scanning laser ophthalmoscopy and spectral domain optical coherence tomography", (N. V. Iftimia, D. X. Hammer, C. E. Bigelow, T. Ustun, J. F. de Boer, and R. D. Ferguson)

SUMMARY OF INVENTION

Problems to be Solved

With the configuration disclosed in Patent Document 1 and Patent Document 4, it is possible to expect efficient light detection and high-contrast image observation using the specular reflection characteristics of the sample material. However, since three sides of a multifaceted mirror are used as the scanning means, there are significant constraints on the optical design with respect to the arrangement of components. Also, since the pupil of the objective lens is split for light projection and light detection, the optical resolution characteristics are disadvantageously restricted.

With the configuration disclosed in Patent Document 2 and Patent Document 3, one can expect a very simple confocal optical system with a single scanning means. However, since a one-dimensional line sensor is used as the detector, the choice of detectors is very limited, and since there are few high-sensitivity detectors, the configuration is not suitable for imaging at low light intensity.

With the configuration disclosed in Non-Patent Document 1, a relatively simple system configuration can be realized by the scanning optical system using the obverse side and reverse side of an oscillating mirror. However, since the reflective surface of the oscillating mirror and the pupil plane of the objective lens are divided in two for light projection and light detection, there are big design constraints, and optical resolution characteristics disadvantageously undergo restriction.

The configuration disclosed in Patent Document 5 reveals the basic technical details of an OCT using an optical fiber interferometer. However, in the configuration disclosed in this document, the scanning means and signal processing system have a slow speed, and, disadvantageously, high-contrast reflection images or fluorescent images as in SLM or SLO cannot be realized in real time.

The configuration disclosed in Patent Document 6 and Patent Document 7 reveals a spectral domain OCT method using a spectrometer in the detection system. This method can advantageously be used to obtain tomographic information at high speed without performing mechanical scanning in the depth direction. However, in the configuration disclosed in these documents, the presence of a reference optical path and a spectrometer disadvantageously render the method unsuitable for dedicated use in high-sensitivity SLM or SLO.

In the configuration disclosed in Patent Document 8, a novel OCT method has been proposed in which scanning means and light modulating means are used efficiently. However, in the configuration disclosed in this document, the presence of a reference optical path and moving means in the direction of the optical axis disadvantageously render the method unsuitable for dedicated use in high-sensitivity SLM or SLO.

In the configuration disclosed in Non-Patent Document 2, a novel optical system combining SLO and OCT has been realized. However, in the configuration disclosed in this document, since a one-dimensional line sensor is used as the detector, the choice of detectors is limited and high-sensitivity imaging is disadvantageously difficult, as are similar to those of the configurations disclosed in Patent Document 2 and Patent Document 3. Also, since the detector is shared by the SLO and OCT systems, the configuration of the members related to the branch in the optical path is complicated, and there are disadvantageously significant optical design constraints.

Therefore, the present invention has been proposed to solve the aforementioned problems, and provides a very practical optical image-capturing apparatus which has fewer design constraints and better optical characteristics than the methods of the prior art, and which, without using no special detectors or optical components, can be used as a dedicated device for SLM or SLO being capable of obtaining high-sensitivity, high-contrast images in real time, and being capable of additionally realizing even OCT measurement functions, if necessary.

Means for Solving the Problems

The present invention relates to an optical image-capturing apparatus in which a light beam from a light source is scanned to illuminate a predetermined portion of an object to be observed, and reflected light or fluorescent light from the object is received to obtain two-dimensional image information of the object.

According to a first aspect of the present invention, there is provided an optical image-capturing apparatus comprising:

a first light source for emitting a light beam;

optical reshaping means for transforming the light beam from the first light source into a slit shape;

an optical path splitting member for introducing the light beam via the optical reshaping means into an optical path towards the object to be observed;

light scanning means for one-dimensionally scanning at a predetermined frequency the light beam introduced via the optical path splitting member;

an objective optical system for guiding the light beam scanned by the light scanning means to the object to be observed and for guiding the reflected light or fluorescent light from the object to be observed;

a light-receiving optical system in which the reflected light or fluorescent light from the object to be observed via the objective optical system is guided through the light scanning means and the optical path splitting member and then through a predetermined detection aperture;

re-scanning means for scanning detection light via the light-receiving optical system at the same scanning frequency and in the same scanning direction as the light scanning means;

two-dimensional image-capturing means for detecting the detection light via the re-scanning means at a frame rate corresponding to a scanning frequency of the light scanning means and the re-scanning means; and measuring means branched or coupled in a relay optical path between the objective optical system and the light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

According to a second aspect of the present invention, the measuring means is detachably constituted in the relay optical path relative to other optical system elements.

According to a third aspect of the present invention, there is provided an optical image-capturing apparatus comprising:

a first light source for emitting a light beam;

optical reshaping means for transforming the light beam from the first light source into a slit shape;

an optical path splitting member for introducing the light beam via the optical reshaping means into an optical path towards the object to be observed;

light scanning means for one-dimensionally scanning at a predetermined frequency the light beam introduced via the optical path splitting member;

an objective optical system for guiding the light beam scanned by the light scanning means to the object to be observed and for guiding the reflected light or fluorescent light from the object to be observed;

a recursive optical system in which the reflected light or fluorescent light from the object to be observed via the objective optical system is guided through the light scanning means and the optical path splitting member and then through a predetermined detection aperture, and is then guided to the light scanning means;

two-dimensional image-capturing means for detecting the detection light via the recursive optical system at a frame rate corresponding to a scanning frequency of the light scanning means; and measuring means branched or coupled in a relay optical path between the objective optical system and the light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

According to a fourth aspect of the present invention, there is provided an optical image-capturing apparatus comprising:

a first light source for emitting a light beam;

optical reshaping means for transforming the light beam from the first light source into a slit shape;

an optical path splitting member for introducing the light beam via the optical reshaping means into an optical path towards the object to be observed;

first light scanning means for one-dimensionally scanning at a predetermined frequency the light beam introduced via the optical path splitting member;

an objective optical system for guiding the light beam scanned by the light scanning means to the object to be observed and for guiding the reflected light or fluorescent light from the object to be observed;

a light-receiving optical system in which the reflected light or fluorescent light from the object to be observed via the objective optical system is guided through the light scanning means and the optical path splitting member and then through a predetermined detection aperture;

second light scanning means for scanning detection light via the light-receiving optical system at the same scanning frequency and in the same scanning direction as the first light scanning means;

two-dimensional image-capturing means for detecting the detection light via the second light scanning means at a frame rate corresponding to a scanning frequency of the first and second light scanning means; and measuring means branched or coupled in a relay optical path between the objective optical system and the first light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

Effect of the Invention

In the configuration of the present invention, two-dimensional image-capturing means has been employed as the detector, and low-speed scanning means and low-speed re-scanning means are used which operate at the frame rate of the image-capturing means. Therefore, the scanning confocal optical system can be simplified, and the electrical controls are also simple.

Since the projected light beam and the received light beam are coaxial in the optical system as the apparatus dedicated for SLMs or SLOs, two-dimensional reflection images (or fluorescent images) with high resolution, sensitivity, contrast, and gradation properties can be obtained at high speeds corresponding to the frame rate of the image-capturing element.

If necessary, a measurement function using an OCT interferometer system can be added. This allows multifunctionality, such as the ability to obtain tomographic image information in the depth direction while obtaining a two-dimensional reflection image (or fluorescent image) of the object.

If a two-dimensional image-capturing element is modified to be more precise, more sensitive, or faster in the future, SLMs and SLOs functions can be improved by simply upgrading the apparatus. In other words, a very practical and economical optical image-capturing apparatus can be realized.

MODE OF CARRYING OUT THE INVENTION

In the following, the present invention will be described in detail based on embodiments shown in the drawings. In the embodiments shown in the following, an object to be observed is exemplified as an ocular fundus of a human eye, and the embodiments of optical systems are shown which are suitable for performing eye examinations. However, the present invention is not limited to these embodiments, and the objects to be observed may also include other biological tissues or living organism samples such as skin with strong light scattering properties.

Embodiment 1

Figure 1:
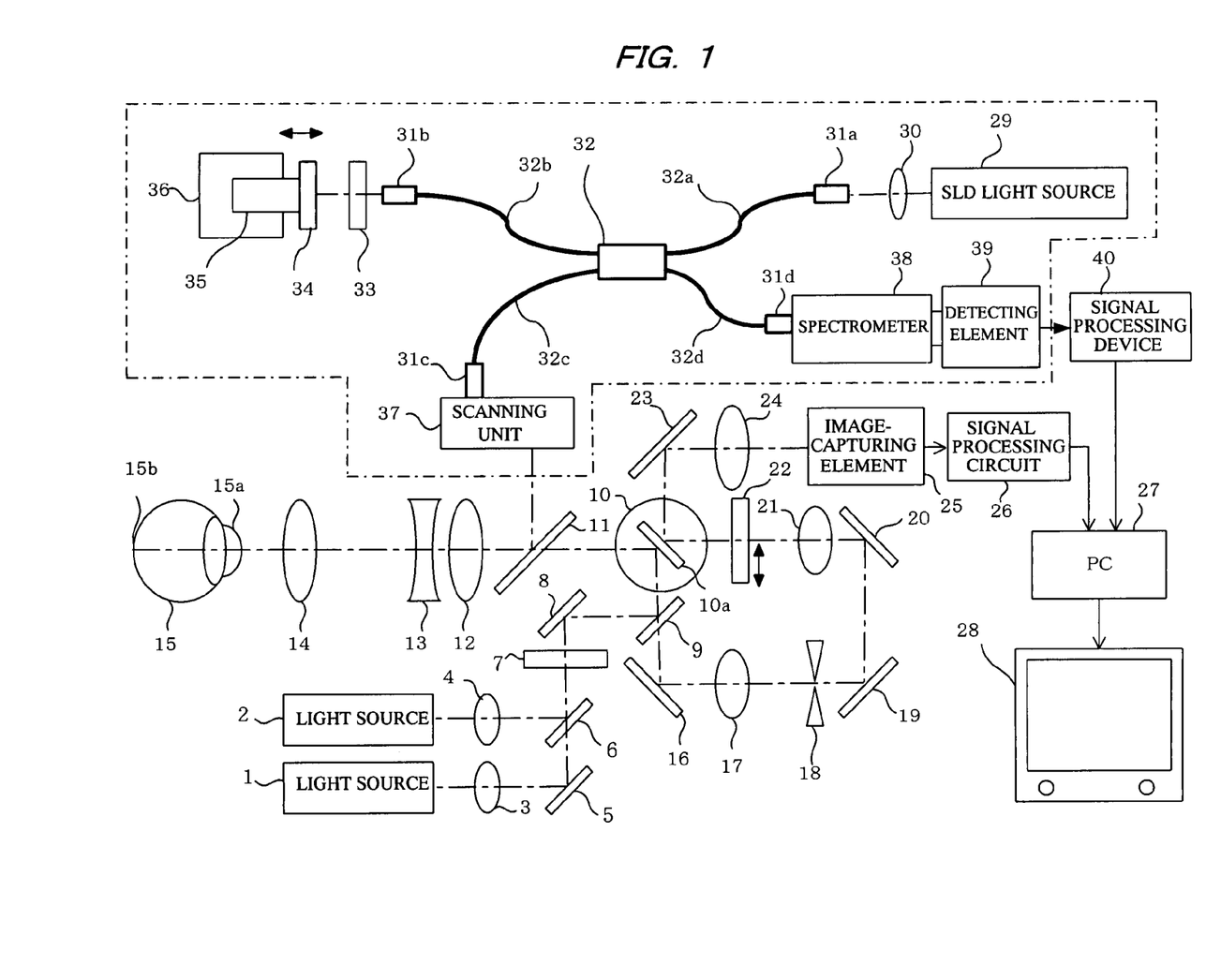
FIG. 1 is a view showing a configuration of the first embodiment of an optical image-capturing apparatus according to the present invention.

In FIG. 1, reference numerals 1 and 2 denote light sources (first light source) used to observe a reflection image or a fluorescent image of an object to be observed. These are predetermined light sources with high luminance such as a light-emitting diode that generates high-luminance light beams (a super luminescent diode or SLD), a semiconductor laser (laser diode), or a solid-state laser. The wavelength is, for example, within a range from approximately 490 nm to 800 nm. Light sources 1 and 2 can be used selectively if necessary in order to use different light beams with different wavelengths as required. The light beams from the light sources 1, 2 are collimated by lenses 3, 4, and combined on the same optical axis via a mirror 5 and a dichroic mirror 6.

The light beam via the mirror 5 and the dichroic mirror 6 is transformed into a flat line beam (a light beam focused linearly on the focal plane) via a cylindrical lens 7, is reflected by a mirror 8, and is made incident on a beam splitter (BS) 9. In other words, the cylindrical lens 7 plays the role of optical reshaping means for transforming the optical beam from the light source into a slit shape. The beam splitter 9 constitutes an optical path splitting member. It can be, for example, a beam splitter having uniform reflection versus transmission characteristics across the entire glass surface, or it can be a partially reflective mirror having characteristics which are reflective in the center and transmissive on the periphery. In the following description, the beam splitter 9 is described as optical path splitting member.

The line beam reflected by the beam splitter 9 is incident on a mirror (galvano mirror) 10a mounted on a galvanometer 10. The galvano mirror 10a performs one-dimensional scanning of the light beam in the direction orthogonal to the optical axis. The scanning by the galvano mirror 10a is performed at a scanning frequency identical to the frame frequency of a typical television camera, for example, 30 Hz (or 60 Hz or another frequency).

The light beam scanned by the galvano mirror 10a is incident on an eye to be examined 15 (anterior ocular segment 15a and ocular fundus 15b) which is an object to be observed, via a dichroic mirror 11, lenses 12, 13, and an objective lens (objective optical system) 14. Here, the lenses 12 and 13 constitute a focusing optical system (focusing means) which can be adjusted in correspondence with the diopter of the eye to be examined (nearsighted or farsighted), and the positions of the lenses 12 and 13 can be adjusted in accordance with the operation of a predetermined mechanism (not shown) in the direction of the optical axis. The lenses 12, 13 and the objective lens 14 constitute a telecentric optical system, which is constituted so that the conjugate relationship between the galvano mirror 10a and the eye to be examined (anterior ocular segment 15a) is kept substantially constant.

The light beam incident on the eye to be examined 15 is focused linearly, for example, at a predetermined position of the ocular fundus 15b. The operation of the galvano mirror 10a (light scanning means) causes the focused line beam to be scanned on the ocular fundus 15b one-dimensionally in the direction (X axis direction) orthogonal to the direction of the beam line (Y axis direction or the direction perpendicular to the plane of the paper in FIG. 1). This allows the ocular fundus 15b of the eye to be examined to be probed two-dimensionally.

The reflected light from the eye to be examined travels back through the above-mentioned optical system, i.e., through the objective lens 14, lenses 13 and 12, the dichroic mirror 11, and the galvano mirror 10a, and reaches the beam splitter 9 (optical path splitting member). The light beam transmitted through the beam splitter 9 is the detection light, which passes through a detection aperture (slit) 18 via a mirror 16 and a lens 17, and is incident on and reflected by the mirror surface on the reverse side of the galvano mirror 10a via mirrors 19, 20, a lens 21, and an optical filter 22.

The optical filter 22 is inserted to detect fluorescent light from the ocular fundus 15b of the eye to be examined. The filter is suitably inserted when needed, as indicated by the arrow in FIG. 1, for example, when naturally occurring fluorescent light from the ocular fundus is detected, or when a fluorescent imaging agent such as sodium fluorescein or ICG (indocyanine green) is used. The detection light via the galvano mirror 10a is reflected by a mirror 23, and projected by a lens 24 onto the imaging surface of a two-dimensional image-capturing element (two-dimensional image-capturing means such as a CCD camera) 25.

In this optical system, the slit 18 has its gap (slit width) restricted in the scanning direction of the galvano mirror 10a. This eliminates noise caused by unwanted stray light and scattered light, and improves the signal-to-noise (SN) characteristics of the detection light. This also reduces the level of background light, efficiently improving the contrast and gradation characteristics of the signal components with respect to video signals from the image-capturing element. The galvano mirror 10a simultaneously serves as the scanning means for scanning the light beam from the light source owing to the reflection action on the obverse side, and also serves as re-scanning means being capable of re-scanning the line beam passing through the slit 18 owing to the reflection action of the reverse side to perform two-dimensional imaging on the imaging surface of the image-capturing element 25.

In other words, the mirror 16, the lens 17, the slit 18, the mirrors 19, 20, and the lens 21 form a recursive optical system that guides the detection light that is once guided via the galvano mirror (light scanning means) 10a and the beam splitter 9 again via the galvano mirror (re-scanning means) 10a to the two-dimensional imaging surface of the image-capturing element 25. In the embodiment as shown in FIG. 1, the galvano mirror 10a is, owing to the reflection action of the obverse surface and reverse surface thereof, regarded as serving as the light scanning means for the projection beam and also serving as the re-scanning means for the detection light.

Next, the output signals from the two-dimensional image-capturing element 25 are sent to a signal processing circuit 26 to perform various types of signal processing related to video signals. The signal processing circuit 26 includes a plurality of electronic circuits for performing signal processing using both analog and digital technologies, such as predetermined amplifier circuits, clamp circuits, buffer circuits, analog-to-digital converters, and various digital signal processing circuits. The processed and generated output signals are then sent to a computer (personal computer or PC) 27.

The PC 27 controls the overall operation of the optical systems (especially the galvanometer 10 and the like), and it also performs controls in which the video signals obtained via the two-dimensional image-capturing element 25 and the signal processing circuit 26 is outputted and displayed on a display device 28 such as a liquid crystal television monitor, and transferred to a predetermined storage device (not shown) for storage, as required.

In the embodiment In FIG. 1, in addition to the optical imaging system described above, measuring means that use an optical fiber interferometer for optical coherence tomography (OCT) (the portion defined by the dashed lines in FIG. 1) is detachably installed in a relay optical path between the objective optical system (14) and the light scanning means (10a).

The reference numeral 29 in FIG. 1 denotes a high-luminance light-emitting diode (super luminescent diode or SLD) that emits partially coherent light. This is the light source (second light source) with the low interference characteristics required for observation of a tomographic image. The light source 29 can be an SLD light source having physical characteristics such as a central wavelength (e.g., 850 nm) different from the central wavelengths of the light sources 1 and 2 and a spectral width of approximately 50 nm. The light beam from the SLD light source 29 is collimated by a lens 30, and then coupled via a coupler 31a to an optical fiber interferometer 32. The optical fiber interferometer 32 has an optical path divided in four directions: a light source optical path 32a, a reference optical path 32b, a probe optical path 32c, and a detection optical path 32d. These optical paths 32a-32d are composed of optical fibers.

The light beam traveling through the reference optical path 32b exits from a coupler 31b, and undergoes intensity adjustment by an ND filter 33. The light beam is then reflected by a mirror 34 and goes back to the reference optical path 32b. The mirror 34 is mounted on a piezoelectric element (piezoelectric transducer) 35, which subtly vibrates the mirror 34 at a predetermined frequency in the direction of the optical axis to perform a periodic phase shift for the light beam. The optical path length of the reference optical path 32b has to be equal to the optical path length of the probe optical path 32c including an optical path towards the eye to be examined. The reflective mirror 34 is accordingly secured on top of a moving stage 36 via the piezoelectric element 35 and is appropriately adjusted if necessary.

On the other hand, the light beam traveling through the probe optical path 32c exits from a coupler 31c, and is incident on a scanning unit 37 including a predetermined galvanometer to perform light beam scanning. The scanning unit 37 includes two galvanometers (not shown), and can perform a desired light beam scanning (linear scanning, circular scanning, and the like) in a direction orthogonal to the optical axis (XY planar direction).

The OCT light beam scanned by the scanning unit 37 is reflected by the dichroic mirror 11, passes through the lenses 12, 13 and the objective lens 14, and is then incident on the eye to be examined 15 (anterior ocular segment 15a or ocular fundus 15b), i.e., the object to be observed. As described earlier, the lenses 12, 13 and the objective lens 14 constitute a telecentric optical system, thereby allowing a configuration in which the conjugate relationship between the scanning unit 37 and the anterior ocular segment 15a of the eye to be examined is kept substantially constant.

Referring to the OCT light beam, the reflected light from the eye to be examined traces back through the optical system described above (objective lens 14, lenses 13 and 12, dichroic mirror 11), and is guided via the scanning unit 37 and the coupler 31c to the optical fiber. The probe light moving through the probe optical path 32c of the optical fiber is combined with the reference light through the reference optical path 32b. This causes interference light (detection light) to be generated on the side of the detection optical path 32d. The detection light emitted from the optical fiber of the detection optical path 32d passes through the coupler 31d and undergoes spectral processing by a spectrometer 38. The detection light is then detected by a one-dimensional CCD line sensor (OCT detecting element) 39, and outputted as electric signals.

The output signals from the CCD line sensor 39 undergo predetermined signal processing such as filter processing via a signal processing device 40, and are then sent to the PC 27. A predetermined software inside the PC carries out predetermined arithmetic processing such as a fast Fourier transform (FFT) required for a spectral domain OCT method, and then calculates tomographic image information from the object to be observed (the eye to be examined). The final results are displayed on the monitor screen of a display device 28 such as a liquid crystal monitor.

FIG. 3A through FIG. 3D are schematic views used to describe the image information obtained via the two-dimensional image-capturing element 25 and the image information obtained via the OCT detecting element 39 in the configuration of FIG. 1 as described above.

Figure 3A:
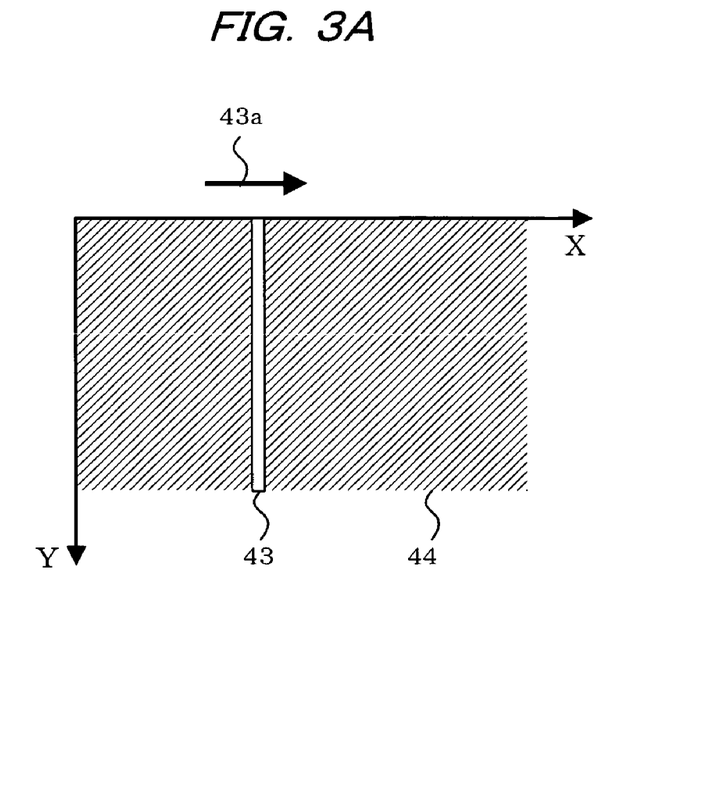
FIG. 3A is an illustrative view showing a process for obtaining image information that is detected and displayed by the optical image-capturing apparatus of the present invention.

In FIG. 3A, the horizontal axis (X axis) corresponds to the horizontal direction of the imaging surface of the two-dimensional image-capturing element 25, and the vertical axis (Y axis) corresponds to the orthogonal direction of the imaging surface. A slit image 43 at a predetermined moment is taken on a dark background 44 on the imaging surface of the image-capturing element 25 by the action of the optical system described above. This slit image 43 moves periodically over time in the direction of the X axis (the direction of arrow 43a) in FIG. 3a in accordance with the scanning performed by the light scanning means (galvano mirror 10a) and the re-scanning means (galvano mirror 10a).

Figure 3B:
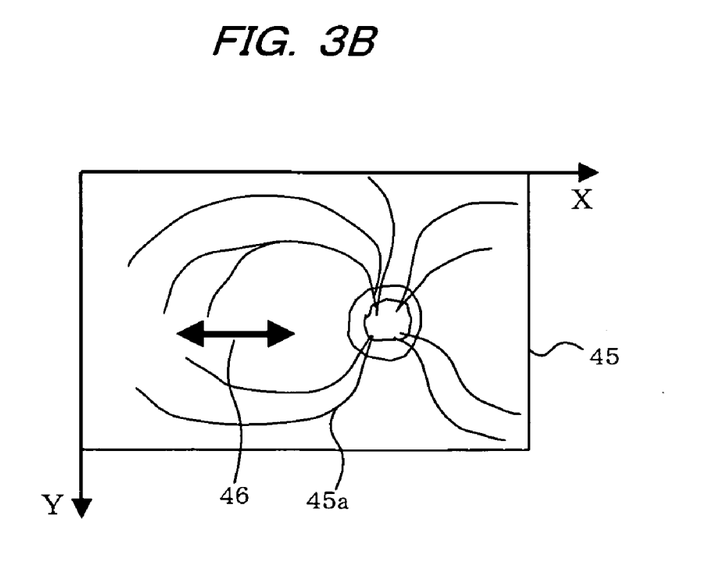
FIG. 3B is an illustrative view showing a tomographic image detected by the optical image-capturing apparatus of the present invention.

Accordingly, image information obtained via the image-capturing element 25 is subjected to various types of signal processing in the signal processing circuit 26, and, as shown in FIG. 3B, a two-dimensional reflection image 45 (when the optical filter 22 is removed from the optical path) or a fluorescent image (when the optical filter 22 is inserted into the optical path) of the object to be observed (e.g., the ocular fundus 15b of the eye to be examined) is obtained. As mentioned above, the reflection (or fluorescent) image 45 is composed of high-contrast video information in which stray light and unwanted scattered light is eliminated from the detection light by the action of the detection aperture (slit 18) in the optical system. FIG. 3B schematically shows a blood vessel pattern 45a in the ocular fundus being imaged. In this drawing, the portion in which tomographic image is to be obtained using the OCT measuring means is indicated schematically by arrow 46.

While viewing the reflection image 45 displayed on the display device 28, the portion 46 in which the tomographic image is to be obtained is designated using input means (not shown) such as an input pen or mouse connected to the PC 27. The coordinate positions of the designated portion (the source and destination in the XY coordinates, or the like) are stored in the memory of the PC 27. The start measurement button (not shown) displayed on the screen of the display device 28 is clicked to start the measurement performed by the OCT measuring means. The output signals from the detecting element 39 are subjected to predetermined signal processing such as filter processing via the signal processing device 40, and then sent to the PC 27. The PC 27 uses a calculation method for spectral domain OCT such as fast Fourier transform (FFT) to determine the depth (Z) information at each coordinate position (X) corresponding to the measurement range designated by the input means, and obtains a tomographic image (XZ image) in the depth direction.

Figure 3C:
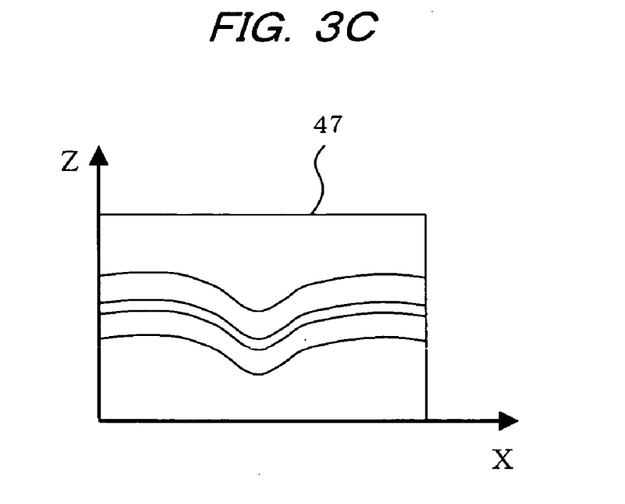
FIG. 3C is an illustrative view showing a reflection image detected by the optical image-capturing apparatus of the present invention.

FIG. 3C schematically shows the tomographic image 47 in the depth direction (XZ image) obtained using the OCT measuring means. This shows image information obtained via the optical fiber interferometer 32 and the detecting element 39. In other words, the tomographic image 47 in the depth direction (XZ image) of the object to be observed (the ocular fundus 15b) can be detected using OCT image information.

Figure 3D:
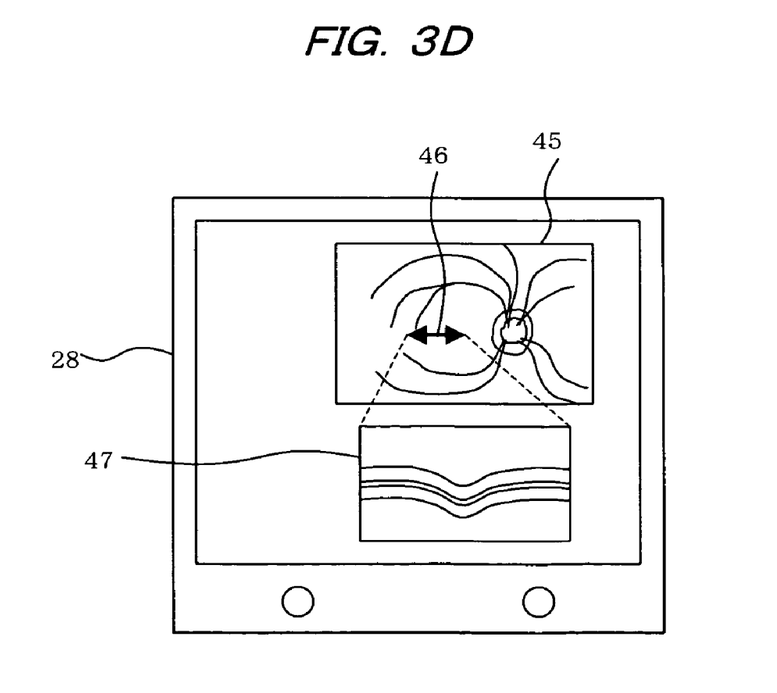
FIG. 3D is an illustrative view showing a tomographic image and a reflection image detected by the optical image-capturing apparatus of the present invention.

FIG. 3D schematically shows the simultaneous display on the monitor screen of the display device 28 with respect to the reflection image 45 (or fluorescent image) obtained via the two-dimensional image-capturing element 25 and the tomographic image 47 (XZ image) obtained via the OCT detecting element 39.

As an example of important applications of OCT in clinical medicine, information obtained from the simultaneous detection of a reflection image (or fluorescent image) and a tomographic image of an ocular fundus can be effectively utilized in precise diagnoses and surgical planning for serious eye diseases such as various types of retinal degeneration and retinal detachment.

Embodiment 2

Figure 2:
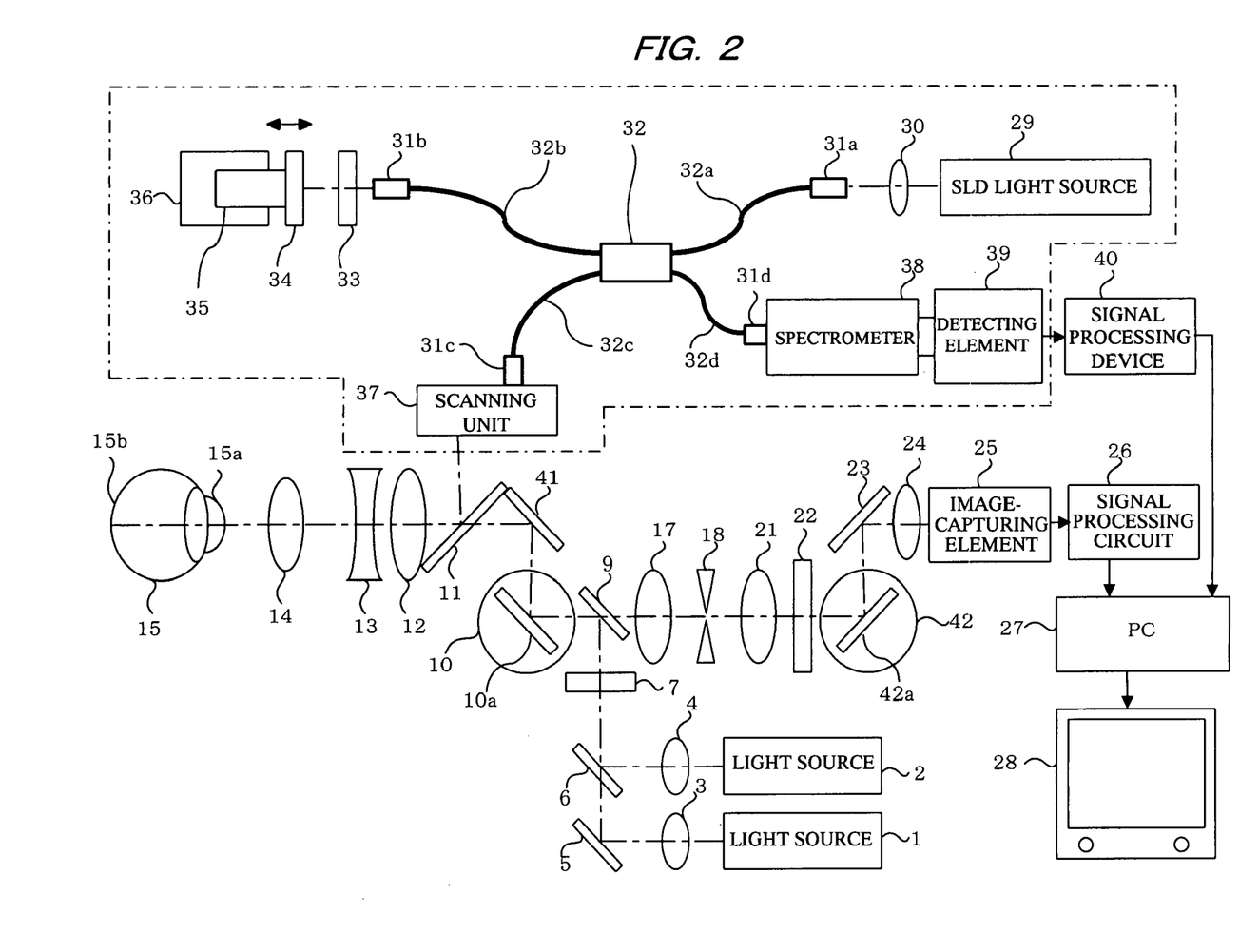
FIG. 2 is a view showing a configuration of the second embodiment of an optical image-capturing apparatus according to the present invention.

FIG. 2 shows a system configuration of the embodiment of the present invention that differs from the embodiment in FIG. 1. In FIG. 2, the object to be observed is also assumed to be a human eyeball (anterior ocular segment or ocular fundus). In FIG. 2, the elements identical to the structural elements in FIG. 1 are denoted by the same reference numerals. The structural elements denoted by the same reference numerals in FIG. 2 have the same configuration and function as those in FIG. 1. The following is primarily a description of the points of difference with FIG. 1.

Light beams from the light sources (SLD or LD) 1, 2 for observing a reflection image or fluorescent image pass through the dichroic mirror 6 and the like, and are shaped by the cylindrical lens 7 into a line beam (slit-shaped beam) which is linear at the focal position. The light beam shaped into a slit is reflected by the beam splitter 9 (BS, optical path splitting member), and then scanned one-dimensionally by the galvano mirror 10a.

The scanned light beam is incident on the eye to be examined 15 (anterior ocular segment 15a or ocular fundus 15b) via a mirror 41, dichroic mirror 11, lenses 12, 13, and objective lens 14. Here, the lenses 12, 13 and the objective lens 14 constitute a telecentric optical system, and the conjugate relationship between the galvano mirror 10a and the anterior ocular segment 15a of the eye to be examined is assumed to be kept substantially constant.

The reflected light from the predetermined portion of the eye to be examined (e.g., the ocular fundus 15b) goes back along the optical path described above, is transmitted through the BS 9, and then passes through the detection aperture (slit) 18 via the lens 17. The detection aperture 18 removes the unwanted noise related to the detection light to improve the SN of the detection signals, and improves the contrast and gradation characteristics of the signals. The light beam that has passed through the detection aperture is guided via the lens 21 and the optical filter 22 to a galvano mirror 42a mounted on a galvanometer 42. The optical filter 22 is inserted into the optical path in order to detect a fluorescent image based on naturally occurring fluorescent light or to detect a fluorescent image when a fluorescent imaging agent is used. The optical filter 22 is removed from the optical path when a reflection image is to be obtained instead of a fluorescent image.

The galvano mirror 42a (second light scanning means) is the re-scanning means for scanning the detection light in the same scanning direction as the galvano mirror 10a (first light scanning means). The scanning frequency is set at the same level for both galvano mirrors 42a, 10a. The detection light re-scanned by the galvano mirror 42a is focused on the two-dimensional image-capturing element 25 such as a CCD via the mirror 23 and the lens 24. In the configuration shown in FIG. 2, the frame rate of the two-dimensional image-capturing element 25 is 60 frames per second, and the scanning frequency of the galvano mirrors 10a, 42a is 60 Hz. In this configuration, as a result, two galvano mirrors are used. The deflecting-back mirrors (16, 19, 20) needed in the configuration of FIG. 1 are not required, and the efficiency of the detection optical system can be improved. Because the configuration of the optical path is simple, optical adjustment is advantageously facilitated as well.

The video signals outputted from the image-capturing element 25 are subjected to predetermined signal processing via the signal processing circuit 26 to extract video signals (for a reflection image, fluorescent image, or the like). The obtained video signals are displayed via the PC 27 on the display means 28 such as a liquid crystal monitor, and can be stored in a storage device (not shown) if necessary. The PC 27 is used to control the image signals and simultaneously controls the overall operation of the optical system (particularly the galvano meters 10 and 42, and the like).

In the embodiment in FIG. 2, in addition to the optical imaging system described above, OCT measuring means using an optical fiber interferometer (shown by the dashed lines in a configuration similar to that shown in FIG. 1) is detachably added to the relay optical path between the objective optical system (14) and the light scanning means (10a).

In FIG. 2, reference numeral 29 denotes a high-luminance light-emitting diode (super luminescent diode or SLD) emitting partially coherent light. This is the light source required for observation of a tomographic image. The light beam from the SLD light source 29 is guided to the optical fiber interferometer 32 via the lens 30. As described with reference to FIG. 1, the optical fiber interferometer 32 has an optical path divided in four directions: a light source optical path 32a, a reference optical path 32b, a probe optical path 32c, and a detection optical path 32d.

The light beam traveling through the reference optical path 32b exits from the coupler 31b, is then reflected by the mirror 34, and goes back to the reference optical path 32b. The optical path length of the reference optical path can be suitably adjusted if necessary using the moving stage 36.

The light beam traveling through the probe optical path 32c exits from the coupler 31c, and is incident on the scanning unit 37 to perform light beam scanning. The OCT light beam scanned by the scanning unit 37 is reflected by the dichroic mirror 11, and is then incident on the eye to be examined 15, which is the object to be observed, via the lenses 12, 13, and the objective lens 14.

Referring to the OCT light beam, the reflected light from the eye to be examined traces back through the optical system described above (objective lens 14, lenses 13 and 12, dichroic mirror 11), and is guided to the optical fiber 32c via the scanning unit 37. The probe light that has passed through the optical fiber serving as the probe optical path 32c is combined with the reference light through the reference optical path 32b. This causes interference light (detection light) to be generated on the side of the detection optical path 32d. The detection light emitted from the optical fiber undergoes spectral processing by the spectrometer 38, detected by the one-dimensional CCD line sensor (OCT detecting element) 39, and outputted as electric signals.

The output signals from the CCD line sensor 39 are sent via the signal processing device 40 to the personal computer (PC) 27. A predetermined software inside the PC carries out predetermined arithmetic processing such as a fast Fourier transform (FFT) required for a spectral domain OCT method, and then calculates the tomographic image information of the eye to be examined 15. The final results are displayed on the monitor screen of the display device 28.

The same operations as those performed in the embodiment shown in FIG. 1 are performed in the embodiment shown in FIG. 2. As shown in FIG. 3A, the slit image 43 is moved periodically over time in the direction of arrow 43a in accordance with scanning by the galvano mirror (scanning means) 10a and the galvano mirror (re-scanning means) 42a. By virtue of the scanning, a two-dimensional reflection image 45 (or fluorescent image) of the object to be observed (e.g., the ocular fundus 15b of an eye to be examined) is obtained via the image-capturing element 25, as shown in FIG. 3B.

As described with reference to the embodiment in FIG. 1, the portion 46 in which tomographic information is to be obtained is designated in the image using the input means. This allows a tomographic image 47 (XZ image) of the object to be observed (the ocular fundus 15b) to be obtained in the depth direction via the OCT measuring means, the signal processing device 40, and the PC 27. In order to compare the reflection image 45 (or fluorescent image) with the tomographic image 47 (XZ image), they can be simultaneously displayed as measurement results on the monitor screen in the display device 28, as shown in FIG. 3D.

As an example of important applications of OCT in clinical medicine, information obtained from the simultaneous detection of a reflection image (or fluorescent image) and a tomographic image of an ocular fundus can be effectively utilized in precise diagnoses and surgical planning for serious eye diseases such as various types of retinal degeneration and retinal detachment. This is the same as in the embodiment in FIG. 1.

KEY TO SYMBOLS

1 Imaging Light Source for Reflection Image (or Fluorescent Image)
7 Cylindrical Lens
9 Beam Splitter
10a, 42a Light Scanning Means or Re-scanning Means (Galvano Mirror)
11 Dichroic Mirror
15 Object to be observed (Eye to be examined)
18 Detection Aperture (Slit)
25 2-Dimensional Image-capturing Element
27 PC
28 Display Means
29 Light Source for OCT
32 Optical Fiber Interferometer
34 Reference Mirror
37 Scanning Unit
38 Spectrometer
39 Detecting Element for OCT

The invention claimed is:

1. An optical image-capturing apparatus in which a light beam from a light source is scanned to illuminate a predetermined portion of an object to be observed, and reflected light or fluorescent light from the object is received to obtain two-dimensional image information of the object, comprising:
a first light source for emitting a light beam;
optical reshaping means for transforming the light beam from the first light source into a slit shape;
an optical path splitting member for introducing the light beam via the optical reshaping means into an optical path towards the object to be observed;
light scanning means for one-dimensionally scanning at a predetermined frequency the light beam introduced via the optical path splitting member;
an objective optical system for guiding the light beam scanned by the light scanning means to the object to be observed and for guiding the reflected light or fluorescent light from the object to be observed;
a light-receiving optical system in which the reflected light or fluorescent light from the object to be observed via the objective optical system is guided through the light scanning means and the optical path splitting member and then through a predetermined detection aperture;
re-scanning means for scanning detection light via the light-receiving optical system at the same scanning frequency and in the same scanning direction as the light scanning means;
two-dimensional image-capturing means for detecting the detection light via the re-scanning means at a frame rate corresponding to a scanning frequency of the light scanning means and the re-scanning means; and
measuring means branched or coupled in a relay optical path between the objective optical system and the light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

2. An optical image-capturing apparatus in which a light beam from a light source is scanned to illuminate a predetermined portion of an object to be observed, and reflected light or fluorescent light from the object is received to obtain two-dimensional image information of the object, comprising:
a first light source for emitting a light beam;
optical reshaping means for transforming the light beam from the first light source into a slit shape;
an optical path splitting member for introducing the light beam via the optical reshaping means into an optical path towards the object to be observed;
light scanning means for one-dimensionally scanning at a predetermined frequency the light beam introduced via the optical path splitting member;
an objective optical system for guiding the light beam scanned by the light scanning means to the object to be observed and for guiding the reflected light or fluorescent light from the object to be observed;
a light-receiving optical system in which the reflected light or fluorescent light from the object to be observed via the objective optical system is guided through the light scanning means and the optical path splitting member and then through a predetermined detection aperture;
re-scanning means for scanning detection light via the light-receiving optical system at the same scanning frequency and in the same scanning direction as the light scanning means;
two-dimensional image-capturing means for detecting the detection light via the re-scanning means at a frame rate corresponding to a scanning frequency of the light scanning means and the re-scanning means; and measuring means branched or coupled in a relay optical path between the objective optical system and the light scanning means, provided with a second light source for emitting a light beam having a wavelength different from that of the first light source, and adapted for obtaining, based on the light beam from the second light source, predetermined image information in a direction different from that of the output information from the two-dimensional image-capturing means, wherein the measuring means is detachably constituted in the relay optical path relative to other optical system elements.

3. An optical image-capturing apparatus in which a light beam from a light source is scanned to illuminate a predetermined portion of an object to be observed, and reflected light or fluorescent light from the object is received to obtain two-dimensional image information of the object, comprising:

a first light source for emitting a light beam:

optical reshaping means for transforming the light beam from the first light source into a slit shape:

an optical path splitting member for introducing the light beam via the optical reshaping means into an optical path towards the object to be observed:

light scanning means for one-dimensionally scanning at a predetermined frequency the light beam introduced via the optical path splitting member:

an objective optical system for guiding the light beam scanned by the light scanning means to the object to be observed and for guiding the reflected light or fluorescent light from the object to be observed:

a recursive optical system in which the reflected light or fluorescent light from the object to be observed via the objective optical system is guided through the light scanning means and the optical path splitting member and then through a predetermined detection aperture, and is then guided to the light scanning means:

two-dimensional image-capturing means for detecting the detection light via the recursive optical system at a frame rate corresponding to a scanning frequency of the light scanning means: and measuring means branched or coupled in a relay optical path between the objective optical system and the light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

4. An optical image-capturing apparatus in which a light beam from a light source is scanned to illuminate a predetermined portion of an object to be observed, and reflected light or fluorescent light from the object is received to obtain two-dimensional image information of the object, comprising:

a first light source for emitting a light beam;

optical reshaping means for transforming the light beam from the first light source into a slit shape;

an optical path splitting member for introducing the light beam via the optical reshaping means into an optical path towards the object to be observed;

first light scanning means for one-dimensionally scanning at a predetermined frequency the light beam introduced via the optical path splitting member;

an objective optical system for guiding the light beam scanned by the light scanning means to the object to be observed and for guiding the reflected light or fluorescent light from the object to be observed;

a light-receiving optical system in which the reflected light or fluorescent light from the object to be observed via the objective optical system is guided through the light scanning means and the optical path splitting member and then through a predetermined detection aperture;

second light scanning means for scanning detection light via the light-receiving optical system at the same scanning frequency and in the same scanning direction as the first light scanning means;

two-dimensional image-capturing means for detecting the detection light via the second light scanning means at a frame rate corresponding to a scanning frequency of the first and second light scanning means; and measuring means branched or coupled in a relay optical path between the objective optical system and the first light scanning means, provided with a second light source for emitting a light beam having a wavelength different from that of the first light source, and adapted for obtaining, based on the light beam from the second light source, predetermined image information in a direction different from that of the output information from the two-dimensional image-capturing means.

* * * * *